United States Patent [19]

Nagano

[11] Patent Number: 4,709,013
[45] Date of Patent: Nov. 24, 1987

[54] GLUTATHIONE MONOALKYL ESTER SULFATES AND PROCESS FOR PRODUCING THE SAME

[75] Inventor: Yoshinobu Nagano, Tokyo, Japan

[73] Assignee: Yamanouchi Pharmaceutical Co., Ltd., Tokyo, Japan

[21] Appl. No.: 869,187

[22] Filed: May 30, 1986

[30] Foreign Application Priority Data

Jun. 7, 1985 [JP] Japan ................................ 60-123930

[51] Int. Cl.$^4$ ........................... C07K 7/02; C07K 5/08
[52] U.S. Cl. ..................................... 530/332; 530/331
[58] Field of Search ................................ 530/331, 332

[56] References Cited

PUBLICATIONS

Chem. Abstr., vol. 62, (1965), 9567h.
Chem. Abstr., vol. 62, (1965), 869c&h.
Chem. Abstr., vol. 86, (1977), 52093c.
Chem. Abstr., vol. 76, (1972), 124283.
Chem. Abstr., vol. 84, (1976), 161001.
Chem. Abstr., vol. 10070c.
Chem. Abstr., vol. 58, (1963), 9471c.
Proc. Natl. Acad. Sci., 80, 5258-60 (1983).

Primary Examiner—Delbert R. Phillips
Attorney, Agent, or Firm—Burgess, Ryan and Wayne

[57] ABSTRACT

Sulfates of glutathione monoalkyl esters (alkyl$\gamma$-L-glutamyl-L-cysteinylglycinates) are new and can be prepared by reaction of glutathione with an alcohol in the presence of sulfuric acid. This process forms virtually no diesters, which are toxic compounds and must be completely removed when the sulfates are used as medicine. In addition, since pure glutathione monoester sulfates can be isolated from reaction mixture, high-purity free glutathione monoesters, which have importance as therapeutical and preventive medicines, can be obtained by treatment with a neutralizer or by mere desalting.

6 Claims, No Drawings

GLUTATHIONE MONOALKYL ESTER SULFATES AND PROCESS FOR PRODUCING THE SAME

BACKGROUND OF THE INVENTION

1. Field of the Invention

This invention relates to novel sulfates of monoalkyl esters of glutathione ($\gamma$-L-glutamyl-L-cysteinylglycine) at the glycine carboxylic acid (hereinafter abbreviated as "glutathione monoester sulfates"), and to a process for producing the same.

2. Description of the Prior Art

An animal test showed that glutathione monoesters, unlike glutathione itself, are able to transfer into many types of cells at high concentrations and undergo hydrolysis in the cells to return back to glutathione [Proc. Natl. Acad. Sci. U.S.A., Vol.80, 5258 (1983)]. Hence glutathione monoesters are useful as easy-to-absorb, active derivatives of glutathione which effectively exhibit in living bodies glutathione's pharmacological activities, such as detoxication and radioprotective effects.

There is no literature discussing acid addition salts of glutathione monoesters (formed by esterification of glutathione by common methods), except the above-mentioned report in which description is made only of hydrochlorides of glutathione monoesters. That report, however, presents no detailed description on how the hydrochlorides had been prepared, but states that these salts were synthesized according to the method shown in Bergmann M. and Zervas L.; Z. Physiol. Chem., Vol.221, 51–54 (1933). Method of Bergmann, et al. is concerned with the synthesis of $\gamma$-ethyl ester of glutamic acid by reaction of the acid with ethanol in the presence of hydrochloric acid. Therefore it may be deduced that the authors of the above-mentioned paper [Proc. Natl. Acad. Sci. U.S.A., Vol.80, 5258 (1983)] prepared the hydrochlorides of glutathione monoesters by direct esterification of glutathione with ethanol (or methanol) in the presence of hydrochloric acid.

Hydrochlorides of glutathione monoesters, however, cannot be isolated as crystals and hence tend to contain diesters as impurity. Diesters of glutathione, unlike monoesters, are toxic compounds and must be completely removed. Sulfates of glutathione monoesters of this invention are novel compounds which are highly crystallizable and hence can be purified very easily. Thus the process of this invention is capable of easily affording pure glutathione monoesters free from such toxic diesters.

PREFERRED EMBODIMENTS OF THE INVENTION

The alkyl groups of the glutathione monoalkylester sulfates of this invention are linear or branched, saturated or unsaturated alkyls of 1 to 10 carbon atoms, and should preferably be linear, saturated alkyls such as methyl, ethyl, butyl, pentyl, hexyl, heptyl, octyl, nonyl and decyl, or branched, saturated alkyls such as isopropyl, isobutyl, sec-butyl, tert-butyl and isopentyl. Of these, ethyl, isopropyl, isobutyl and n-hexyl are most preferred.

Glutathioone produced by any methods may be used as the starting material for the chemical synthesis of glutathione monoester sulfates; namely, glutathione extracted and isolated from natural products, glutathione prepared by chemical synthesis, or glutathione obtained by genetic techniques may be employed.

Glutathione monoalkyl ester sulfates of this invention can be prepared by reaction of glutathione with an alcohol in the presence of sulfuric acid to esterify the glycine carboxylic acid according to the following reaction scheme:

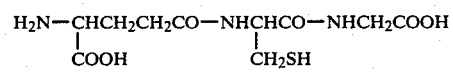

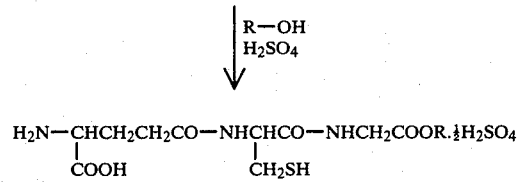

This reaction is effected by adding sulfuric acid to a mixture of glutathione and at least a stoichiomteric amount of an alcohol (R—OH) with stirring. Sulfuric acid of relatively high concentration (for example commercial conc. sulfuric acid) is preferably used. Its suitable amount is 2 to 4 equivalent proportions based on the glutathione used; for the synthesis of isopropyl ester, in particular, use of about 3.5 equivalent proportions is most preferred.

The reaction proceeds smoothly at room temperature. Although some heat is generated during reaction, there is no need for external cooling. A clear solution is obtained in about one hour, and further stirring separates out a glutathione monoester sulfate as crystals. Pure product can be isolated by collecting the crystals by filtration.

The product thus obtained is the sulfate of a monoester of glutathione at its glycine carboxyl group and contains practically no diester as impurity.

There is no specific limitation upon the type of alcohols to be used for the above-described monoesterification, but linear or branched alkyl alcohols of 1 to 10 carbon atoms are preferably employed. Illustrative examples include methanol, ethanol, isopropanol, propanol, butanol and hexanol.

The glutathione monoester sulfates thus prepared can be administered as such to human bodies together with a suitable neutralizing agent, or in the form of free monoester after removal of sulfuric acid. Use of an ion-change resin, for example HP-20 (product of Mitsubishi Chemical Industries), is convenient to release sulfuric acid from sulfate to give free glutathione monoester. A sulfate is charged in a column packed with HP-20, the column is first treated with water to wash off freed sulfuric acid, and the adsorbed glutathione monoester is eluted with 50% aqueous solution of methanol (or ethanol). The monoester is concentrated within a narrow fraction range in pure form, and hence can be efficiently isolated by concentration of the colected elute.

The glutathione monoester sulfates obtained above may be dissolved in water or physiological saline in the presence of a neutralizing agent to give solutions for parenteral or oral administration, or may be mixed with a pharmacologically acceptable carrier (water, lactose, etc.) to afford other types of prepartions.

The suitable daily dose of glutathione monoester sulfates is in the range from 1 micromole to 1 millimole per Kg body weight (in the form of free monoester), preferably in the range from 10 to 100 micromoles, which is subdivided in 1 to 6 doses. The toxicity of glutathione monoesters is extremely low, $LD_{50}$ of glutathione isopropyl ester being about 13 millimole/Kg when it is peritoneally injected into mice.

Virtually no diester is formed in the process of this invention, in contrast to the case glutathione monoester hydrochlorides in which esterification is effected in the presence of hydrochloric acid. In addition, since pure glutathione monoester sulfates can be isolated from the reaction mixture, high-purity free glutathione monoesters, which have importance as a therapeutical and preventive medicine, can be obtained by treatment with a neutralizer or merely by desalting.

EXAMPLE 1

To a mixture of 124 g glutathione and 800 ml isopropanol was added dropwise 42 ml of 95% sulfuric acid with stirring. The reaction was exothermic, but there was no need for external cooling. The mixture turned clear in about one hour, sulfate of glutathione monoisopropyl ester (isopropyl γ-L-glutamyl-L-cisteinyl-glycinate) began to separate out as crystals in about 24 hours, and stirring was further continued overnight. The crystals which separated out were collected by filtration, washed with 200 ml isopropanol and vacuum-dried, giving 88.5 g of crude product.

(1) Part of the crude crystals collected above was recrystallized from a mixture of water and isopropanol (1:5), and the pure crystals thus obtained were submitted to analysis.

(i) M.p. 145°–150° C.

(ii) Elemental analysis (as $C_{13}H_{23}N_3O_6S.\frac{1}{2}H_2SO_4.\frac{1}{2}H_2O$)

|  | C | H | N | S |
|---|---|---|---|---|
| Calcd. (%) | 38.32 | 6.18 | 10.31 | 11.80 |
| Found (%) | 38.11 | 6.34 | 10.32 | 12.10 |

(2) The crude crystals of sulfate collected above (5.0 g) were dissolved in 20 ml of a water/ethanol mixture (1:1) by heating at 80° C. for five minutes, and the solution was filtered and cooled on ice. The crystals which separated out were collected by filtration 60 minutes later, washed with 10 ml ethanol and vacuum-dried, affording 4.4 g of pure cyrstals of sulfate.

(i) M.p. 148°–150° C.

(ii) $[\alpha]_D^{20}$ −15.5 (c=1.0, $H_2O$)

(iii) Elemental analysis (as $C_{13}H_{23}N_3O_6S.\frac{1}{2}H_2SO_4.\frac{1}{2}H_2O$)

|  | C | H | N | S |
|---|---|---|---|---|
| Calcd. (%) | 38.32 | 6.18 | 10.31 | 11.80 |
| Found (%) | 38.37 | 6.06 | 10.14 | 11.78 |

(iv) Mass spectrum FAB: 350

(v) NMR spectrum (DMSO-$d_6$, δ) 1.20 (6H, d, J=6 Hz); 1.76–2.16 (2H, m); 2.20–2.48 (2H, m); 2.60–2.96 (2H, m); 3.48–3.72 (1H, m); 3.78 (2H, d, J=6 Hz); 4.24–4.56 (1H, m); 4.72–6.12 (1H, m).

EXAMPLE 2

To a mixture of 99.2 g glutathione and 400 ml ethanol was added dropwise 24 ml of 95% sulfuric acid with stirring over a period of 15 minutes under ice cooling, and stirring was continued for additional 45 minutes. After the mixture was further stirred at room temperature overnight and then placed in a refrigerator overnight, the crystals which separated out were collected by filtration, washed with 200 ml ethanol and vacuum-dried, giving 50.3 g of crude crystals of glutathione monoethyl ester sulfate.

The crude crystals (45.3 g) were dissolved in 100 ml of a water/ethanol mixture (1:1) by heating at 80° C. for 15 minutes, and the solution was filtered and cooled on ice. The crystals which separated out were collected by filtration 60 minutes later, washed with 70 ml ethanol and vacuum-dried, affording 34.1 g of pure crystals of sulfate.

(i) M.p. 135°–138° C.

(ii) $[\alpha]_D^{25}$ −16.1 (c=1.0, $H_2O$)

(iii) Elemental analysis (as $C_{12}H_{21}N_3O_6S.\frac{1}{2}H_2SO_4.\frac{1}{2}H_2O$)

|  | C | H | N | S |
|---|---|---|---|---|
| Calcd. (%) | 36.63 | 5.89 | 10.68 | 12.23 |
| Found (%) | 36.57 | 6.09 | 10.61 | 12.21 |

(iv) Mass spectrum FAB: 336

(v) NMR spectrum (DMSO-$d_6$, δ): 1.20 (3H, t, J=7 Hz); 1.80–2.16 (2H, m); 2.20–2.48 (2H, m); 2.60–2.96 (2H, m); 3.48–3.72 (1H, m); 3.82 (2H, d, J=6 Hz); 4.10 (2H, q, J=7 Hz); 4.24–4.56 (1H, m).

REFERENCE EXAMPLE 1 (formation of free ester)

The crude sulfate obtained in Example 1 (50.0 g) was dissolved in 1.2 liters of water, and this solution was charged in a column packed with 1.5 liters of HP-20. After the column was washed with water, the adsorbed ester was eluted with a mixture of water and methanol (1:1), and 2.5 liters of fractions containing the desired compound were collected. After concentrating the combined fractions, the residue was freeze-dried, giving 33.8 g of glutathione monoisopropyl ester.

(i) M.p. 184°–186° C.

(ii) IR spectrum (KBr, cm$^{-1}$); 1730, 1635, 1525, 1400, 1370, 1205, 1100.

(iii) Specific rotation $[\alpha]_D^{21}$; −31.0 (c=1.0, $H_2O$)

(iv) NMR spectrum (DMSO-$d_6$, δ): 1.20 (6H, d, J=6 Hz); 1.72–2.16 (2H, m); 2.20–2.40 (2H, m); 2.64–2.86 (2H, m); 3.20–3.56 (1H, m); 3.80 (2H, s); 4.20–4.60 (1H, m); 4.68–5.08 (1H, m).

REFERENCE EXAMPLES 2 THROUGH 5

The following glutathione monoesters can be prepared in the same manner as Reference Example 1.

REFERENCE EXAMPLE 2

Glutathione monomethyl ester (methyl γ-L-glutamyl-L-cysteinylglycinate)

(i) IR spectrum (KBr, cm$^{-1}$): 1740, 1635, 1520, 1400, 1210.

(ii) Specific rotation $[\alpha]_D^{25}$: −32.0 (c=1.0, $H_2O$).

(iii) NMR spectrum (DMSO-$d_6$+$CD_3OD$, δ): 1.72–2.04 (2H, m); 2.20–2.40 (2H, m); 2.64–2.88 (2H, m);

3.16–3.40 (1H, m); 3.60 (3H, s); 3.80 (2H, s); 4.20–4.60 (1H, m).

REFERENCE EXAMPLE 3

Glutathione monoethyl ester (ethyl γ-L-glutamyl-L-cysteinylglycinate)

(i) IR spectrum (KBr, cm$^{-1}$): 1735, 1635, 1520, 1400, 1200.
(ii) Specific rotation $[\alpha]_D^{21}$: −27.2 (c=1.0, H$_2$O).
(iii) NMR spectrum (DMSO-d$_6$, δ): 1.16 (3H, t, J=7); 1.70–2.04 (2H, m); 2.16–2.40 (2H, m); 2.60–2.82 (2H, m); 3.16–3.40 (1H, m); 3.80 (2H, s); 4.04 (2H, q, J=7); 4.20–4.48 (1H, m).

REFERENCE EXAMPLE 4

Glutathione monoisobutyl ester (isobutyl γ-L-glutamyl-L-cysteinylglycinate)

(i) M.p. 188°–190° C.
(ii) IR spectrum (KBr, cm$^{-1}$): 1740, 1635, 1530, 1400, 1200, 1095.
(iii) Specific rotation $[\alpha]_D^{26}$: −24.5 (c=1.0, H$_2$O).
(iii) NMR spectrum (DMSO-d$_6$, δ): 0.88 (6H, d, J=6 Hz); 1.60–2.12 (3H, m); 2.12–2.44 (2H, m); 2.60–3.00 (2H, m); 3.16–3.44 (1H, m); 3.60–4.04 (3H, m); 4.20–4.60 (1H, m).

REFERENCE EXAMPLE 5

Glutathione mono-n-hexyl ester (n-hexyl γ-L-glutamyl-L-cysteinylglycinate)

(i) IR spectrum (KBr, cm$^{-1}$): 1740, 1635, 1520, 1400, 1340, 1300, 1200, 1090.
(ii) Specific rotation $[\alpha]_D^{26}$: −25,2 (c=1.0, MeOH).
(iii) NMR spectrum (DMSO-d$_6$, δ): 0.60–1.04 (3H, m); 1.04–1.76 (8H, m); 1.76–2.16 (2H, m); 2.16–2.48 (2H, m); 2.60–3.04 (2H, m); 3.20–3.56 (1H, m); 3.82 (2H, s); 3.92–4.20 (2H, m); 4.20–4.60 (1H, m).

REFERENCE EXAMPLE 6 (parenteral injection)

Sulfate of glutathione monoisopropryl ester was suspended in purified water at a concentrtion of 45 mg/ml and this suspension was cooled below 5° C. Approximately two molar proportions, based on the ester sulfate, of sodium bicarbonate was added to bring the mixture into solution, the solution thus obtained was adjusted to a pH 4.0 and to a concentration of 40 mg/ml, and filtered germfree. The filtrate was dispensed into vials (each containing 25 ml), followed by freeze drying.

What is claimed is:

1. Sulfates of glutathione monoalkyl esters represented by the following general formula

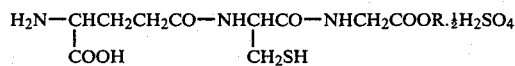

wherein R stands for an alkyl group of 1 to 10 carbon atoms.

2. Sulfates of glutathione monoalkyl esters as defined in claim 1 wherein R is a lower alkyl of 1 to 4 carbon atoms.

3. Sulfates of glutathione monoalkyl esters as defined in claim 1 wherein R is ethyl.

4. Sulfates of glutathione monoalkyl esters as defined in claim 1 wherein R is isopropyl.

5. A process for producing sulfates of glutathione monoalkyl esters represented by the following general formula

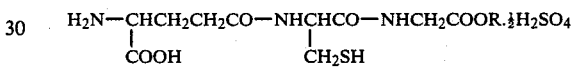

wherein R stands for an alkyl group of 1 to 10 carbon atoms, which comprises reaction of γ-L-glutamyl-L-cysteinylglycine with an alcohol of formula R—OH wherein R is as defined above in the presence of sulfuric acid.

6. The process as defined in claim 5 wherein the reaction is carried out in the presence of sulfuric acid in an amount of 2 to 4 equivalent proportions based on γ-L-glutamyl-L-cysteinylglycine.

* * * * *